United States Patent [19]
Ferro et al.

[11] Patent Number: 5,869,674
[45] Date of Patent: Feb. 9, 1999

[54] ARYLPYRAZOLES AS LEUKOTRIENE INHIBITORS

[75] Inventors: Michael P. Ferro, Bridgewater; Michael P. Wachter, Bloomsbury, both of N.J.

[73] Assignee: Ortho Pharmaceutical Corporation, Raritan, N.J.

[21] Appl. No.: 112,114

[22] Filed: Jul. 8, 1998

Related U.S. Application Data

[60] Provisional application No. 60/031,957, Nov. 27, 1996.

Related U.S. Application Data

[62] Division of Ser. No. 977,210, Nov. 24, 1997.
[51] Int. Cl.[6] .................................................. C07D 401/14
[52] U.S. Cl. ........................................ 546/174; 348/377.1
[58] Field of Search .............................................. 546/174

[56] References Cited

U.S. PATENT DOCUMENTS 4,898,952   2/1990   Murray et al. ........................ 548/375.1

OTHER PUBLICATIONS

Structure–Activity Relationships in the Quinoline-Containing Class of Inhibitors of 5–Lipoxygenase Enzyme Translocation and Activation, A.F. Freft, L.A. Marshall, and A. Wong, Drugs of the Future, 1994, 19(3): 255.

5–Lipoxygenase: Properties, Pharmacology, and the Quinolinyl (Bridged) Aryl Class of Inhibitors, J.H. Musser and A. F. Kreft, J. Med. Chem., vol. 35, No. 14, 2501 (1992) and references therein.

A New Class of Leukotriene Biosynthesis Inhibitors: The Discovery of MK0591, P. Prasit, M. Belley, C. Brideau, C. Chan, S. Charleson, J.F. Evans, R. Fortin, A. W. Ford–Hutchinson, S. Leger, D. Riendeau, R. N. Young, and R. Zamboni, Bioorganic & Medicinal Chemistry Letters, vol. 2, No. 12, 1699, 1992.

Development of L–689,065—The Prototype of a New Class of Potent 5–Lipoxygenase Inhibitors, J. H. Hutchinson, P. Prasit, L. Y. Choo, D. Riendeau, S. Charleson, J. F. Evans, H. Piechuta, G. G. Ball, Bioorganic & Medicinal Chemistry Letters, vol. 2, No. 12, 1699, 1992.

Flap: A Novel Drug Target for Inhibiting the Synthesis of Leukotrienes, A. W. Ford–Hutchinson, Trends Pharmacol. Sci., 12, 68 (1991).

A New Class of Leukotriene Biosynthesis Inhibitors: The Development of ((4–(Chlorophenyl)–1–(4–(2–Quinolyl-methoxy)Phenyl)Butyl)Thio)Acetic Acid, L–674,636, P. Prasit, M. Belley, J. F. Evans, J. Y. Gauthier, C. Leveille, C. S. McFarlane, E. MacIntyre, L. Peterson, H. Piechuta, M. Therien, R. N. Young, and R. Zamboni.

Discovery of Inhibitors of the 5–Lipoxygenase Activating Protein (Flap), R. N. Young, J. W. Jillard, J. H. Hutchinson, S. Leger, and P. Prasit, Can. J. Lipid Mediators, (1993), 6 (1–3), 2338.

Clinical and Biochemical Effects of an Oral Leukotriene Biosynthesis Inhibitor (MK886) In Psoriasis, Skin Pharmacol 1991; 4:278–285, E. M. G. J. DeJong, I.M.M. J. Van Vlijmen, J.C. M. Scholte, A. Buntinx, B. Friedman, W. Tanaka, P. C. M. Van De Kerkhof.

*Primary Examiner*—Robert W. Ramsuer
*Attorney, Agent, or Firm*—Kenneth J. Dow

[57] ABSTRACT

Compounds of Formula I

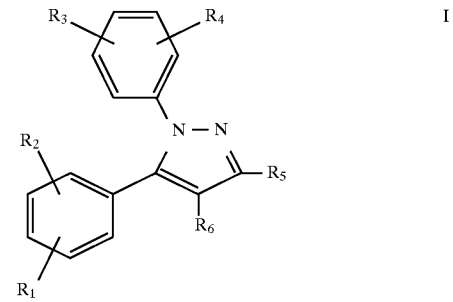

useful in the treatment of inflammatory disorders.

1 Claim, No Drawings

ARYLPYRAZOLES AS LEUKOTRIENE INHIBITORS

This application is a divisional of Ser. No. 08/977,210 filed Nov. 24, 1997 which claims the benefit of provisional application 60/031,957 filed Nov. 27, 1996.

This invention relates a series of arylpyrazoles, intermediates used in their manufacture and pharmaceutical compositions containing them. The compounds are inhibitors of leukotrienes, particularly they inhibit 5-lipoxygenase and may be used in a variety of inflammatory related disorders such as rheumatoid arthritis, asthma, hypersensitivity, myocardial ischemia, psoriasis and inflammatory bowel syndrome.

BACKGROUND OF THE INVENTION

Leukotrienes are a family of endogenous metabolites of arachidonic acid and play an integral role in regulating inflammatory events. Since their discovery in the late seventies, many have worked to determine the biosynthesis of leukotrienes with an eye toward mediating the inflammatory responses. The focus of much of this work concerned the enzymes used in leukotriene biosynthesis, particularly the first enzyme in the cascade, 5-lipoxygenase. This work has produced a number of drug candidates including the anti-asthmatic, zileuton, which is currently in clinical trials.

In the nineties, work surrounding the search for 5-lipoxygenase inhibitors expanded with the discovery of the 5-lipoxygenase activating protein, FLAP. FLAP is a membrane protein which enhances the catalytic activity of 5-lipoxygenase. Although the precise mechanism of this cooperation is unknown, it has been shown that compounds which bind to FLAP, inhibit the action of 5 lipoxygenase in whole cell assays but are inactive in broken cell enzyme assays. This work has lead to a number of interesting compounds, including MK-0591, an anti-asthmatic agent.

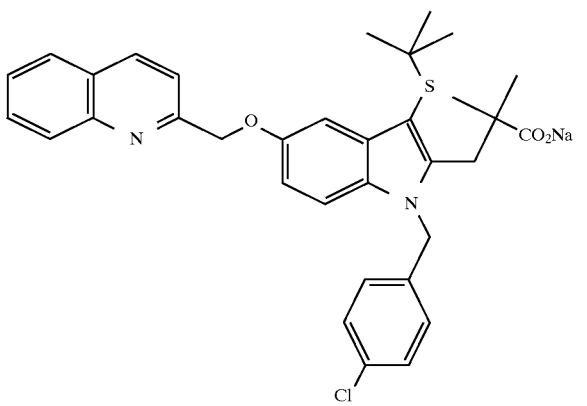

MK-0591

The compounds of the invention are potent 5-lipoxygenase inhibitors many of which are significantly more potent in whole cell assays, than in broken cell enzyme assays. Like other 5-lipoxygenase inhibitors these compounds are useful in the treatment of disease states associated with inhibition of leukotriene biosynthesis such as rheumatoid arthritis, asthma, hypersensitivity, myocardial ischemia, psoriasis and inflammatory bowel syndrome.

SUMMARY OF THE INVENTION

The inventions relates to novel compounds of the Formula I

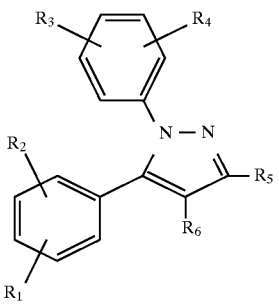

wherein:
$R_1$, $R_2$, $R_3$, and $R_4$ are selected from the group consisting of hydrogen, $C_{1-5}$alkyl, $C_{1-5}$-salkoxy, phenyl, halo, hydroxy, $C_{1-5}$alkylsulfonyl, $C_{1-5}$alkylthio, trihalo$C_{1-5}$salkyl, amino, nitro and 2-quinolinylmethoxy;

$R_5$ is selected from the group consisting of $C_{1-5}$alkyl and $R_7$ where $R_7$ is $(CH_2)_nR_8$ or $(CH_2)_nCHR_8R_9$ where n is 1 or 2;

$R_8$ is halo, oxy, carbonyl, hydroxy, oximino, carboxy, $C_{1-5}$alkoxycarbonyl, N—$C_{1-5}$alkyl-N-hydroxyamido;

$R_9$ is 4-(2-quinolinylmethoxy)phenyl;

$R_6$ is selected from the group consisting of hydrogen, $C_{1-5}$alkyl and halo;

with the proviso that if $R_9$ is present, $R_1$, $R_2$, $R_3$, and $R_4$ are other than 2-quinolinylmethoxy;

with the further proviso that if $R_9$ is absent one of $R_1$, $R_2$, $R_3$, and $R_4$ is 2-quinolinylmethoxy;

and pharmaceutically acceptable salts therof.

An additional formula of the invention is Formula II

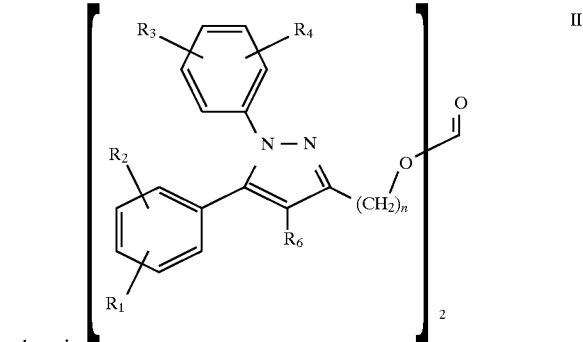

wherein:
$R_1$, $R_2$, $R_3$, and $R_4$ are selected from the groups consisting of hydrogen, $C_{1-5}$alkyl, $C_{1-5}$alkoxy, phenyl, halo, hydroxy, $C_{1-5}$alkylsulfonyl, $C_{1-5}$alkylthio, trihalo$C_{1-5}$ssalkyl, amino, nitro and 2-quinolinylmethoxy;

n is 1–3;

$R_6$ is selected from the group consisting of hydrogen, $C_{1-5}$alkyl and halo;

with the proviso that one of $R_1$, $R_2$, $R_3$, and $R_4$ is 2-quinolinylmethoxy and pharmaceutically acceptable salts thereof.

DETAILED DESCRIPTION OF THE INVENTION

The compounds of Formula I may be prepared as illustrated by the following schemes. As illustrated by Scheme 1 to prepare a compound where $R_1$ is H, $R_2$ is Cl, $R_3$ is hydrogen, $R_4$ is 2-quinolinylmethoxy, $R_5$ is $(CH_2)_2CO_2Et$ and $R_6$ is hydrogen, 3-[5-(4-chlorophenyl)-1-(4-methoxyphenyl)-3-pyrazoloyl]propionic acid 1A is the starting material. This starting material is prepared as described in U.S. Pat. No. 4,826,868 which is hereby incorporated by reference. Acid 1A is treated with HBr to give the hydroxy derivative 1B. 1B may be esterified in the presence of ethanol and $H_2SO_4$ at reflux over 16 h and gives the corresponding ester 1C. Treatment of 1C with 2-(chloromethyl)quinoline and a base such as $K_2CO_3$ in an inert solvent such as acetone at reflux over 16 h gives 1D where $R_1$ is H, $R_2$ is Cl, $R_3$ is hydrogen, $R_4$ is 2-quinolinylmethoxy $R_5$ is $(CH_2)_2CO_2Et$.

SCHEME 1

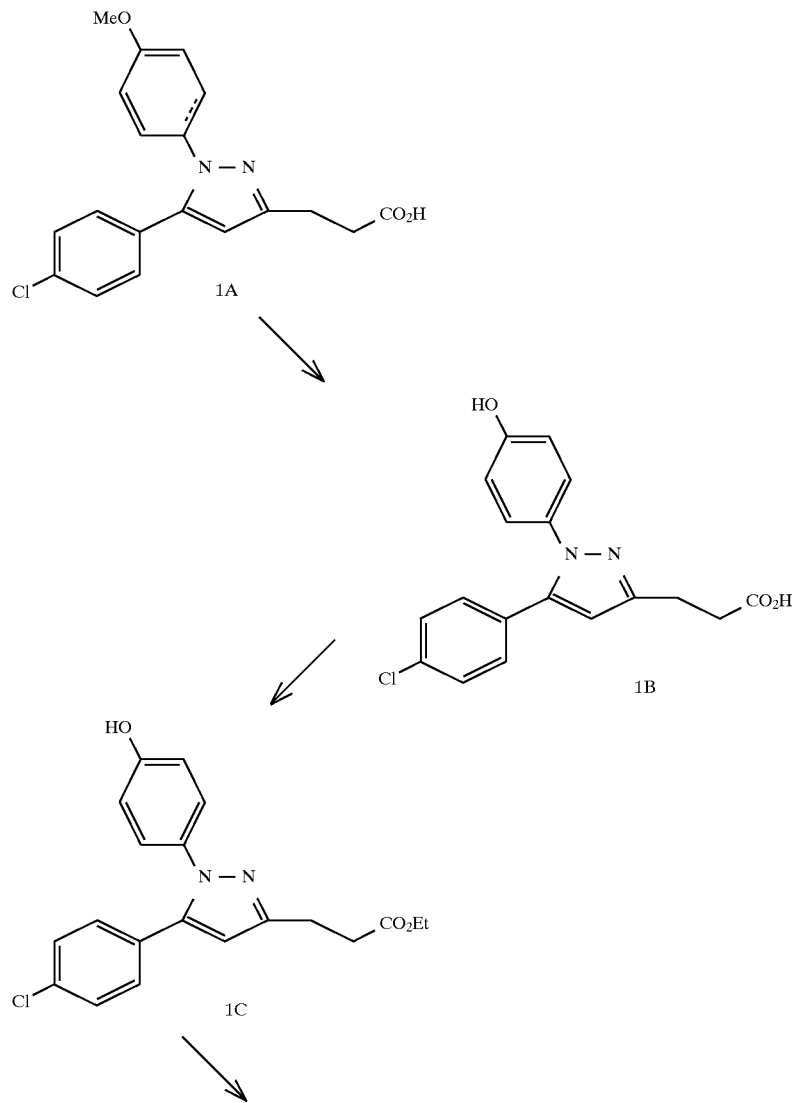

-continued
SCHEME 1

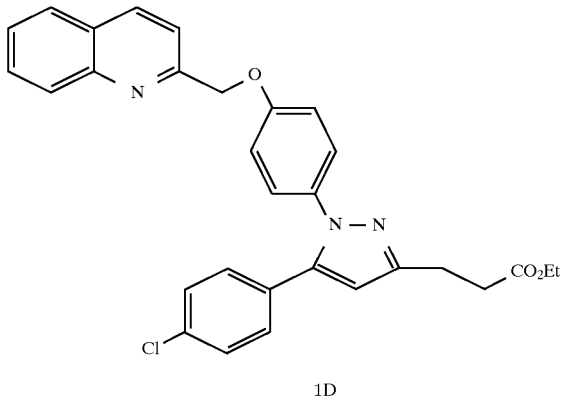

1D

Compound 1D may be used to prepare other compounds of Formula 1 where $R_5$ is $(CH_2)_2CO_2$-i-butyl, $(CH_2)_3OH$ and $(CH_2)_2CO_2H$, as illustrated by Scheme 2. Compound 1D may be hydrolyzed using bases such as NaOH (1.5 eq.) and alcohols such as ethanol to give the corresponding acid 2A. Treatment of 1D with 1M DIBAL (3 eq.) in an inert solvent at about 0° C. for 1–3 h gives the corresponding alcohol 2B. In addition, treatment of 1D with 1M DIBAL/THF (3 eq.) in THF at 0° C. to room temperature over about 16 h gives the isobutyl ester 2C.

SCHEME 2

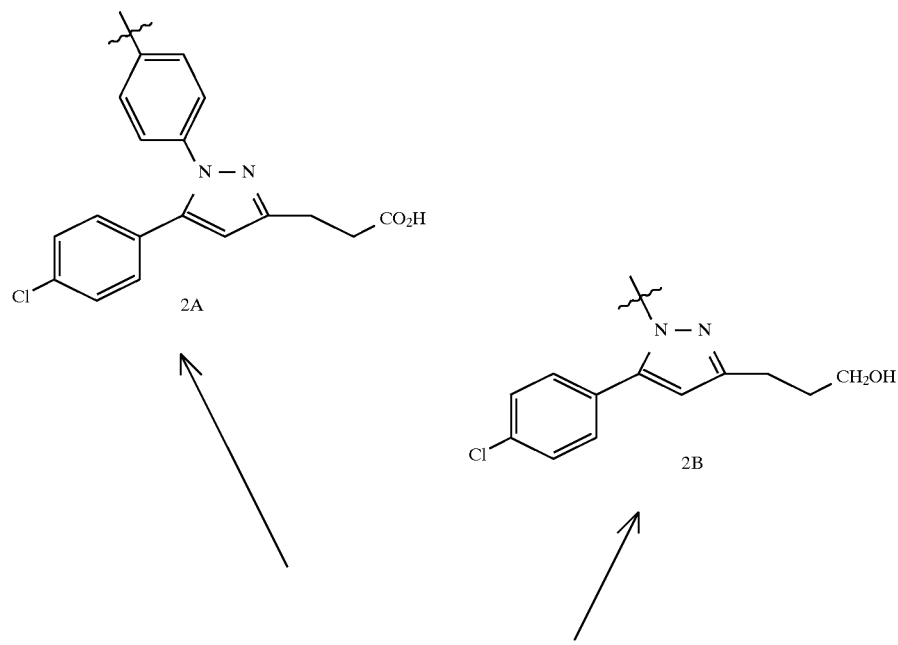

-continued
SCHEME 2

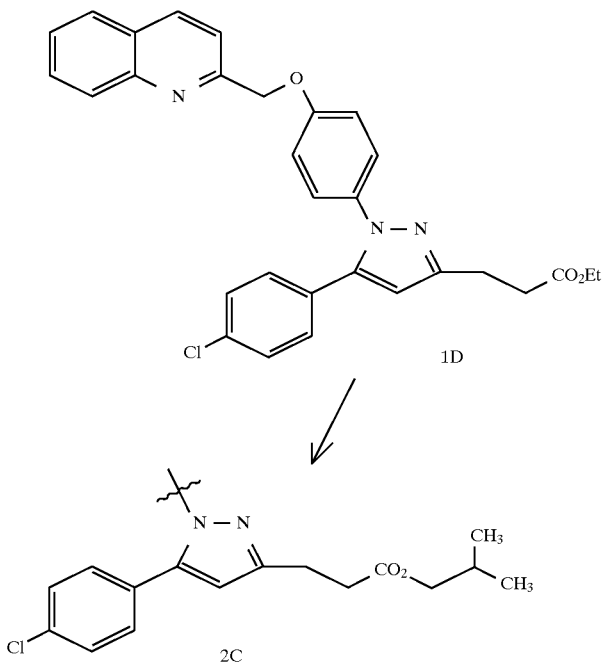

Compounds synthesized by Scheme 2 can be used to prepare other compounds of the invention,. As illustrated by Scheme 3, treatment of the alcohol 2B with triphosgene (ca. 0.5 eq.) and pyridine (ca. 1 eq.) $CH_2Cl_2$ at 0° C. to room temperature for about 1 h, followed by treatment of the resulting mixture with N-methylhydroxylamine hydrochloride (2 eq.) and triethylamine (2 eq.) from 0° C. to room temperature for about 16 h gives the corresponding chloride 3A and the corresponding carbamate 3B. In addition, alcohol 2B may be treated with triphosgene (ca. 0.5 eq.) in pyridine at 0° C. over 3 h, followed by treatment of the resulting mixture with N-methylhydroxylamine hydrochloride (4 eq.) and triethylamine (4 eq.) in $CH_2Cl_2$ at room temperature over 7 days to give the corresponding carbonate 3C. Finally, oxidation of 2B with pyridinium chlorochromate (2 eq.) at room temperature over about 2 h gives the corresponding aldehyde 3D.

SCHEME 3

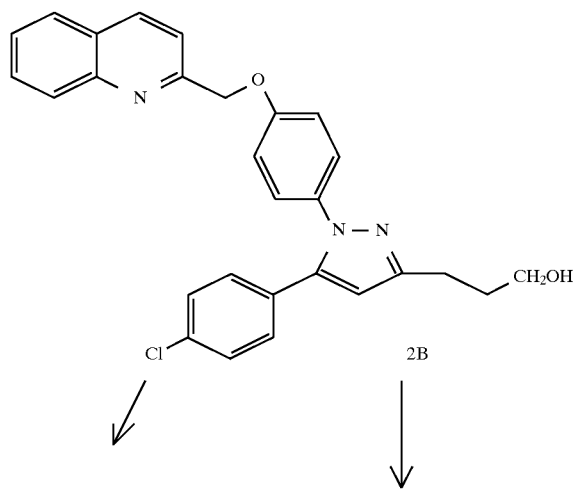

-continued
SCHEME 3

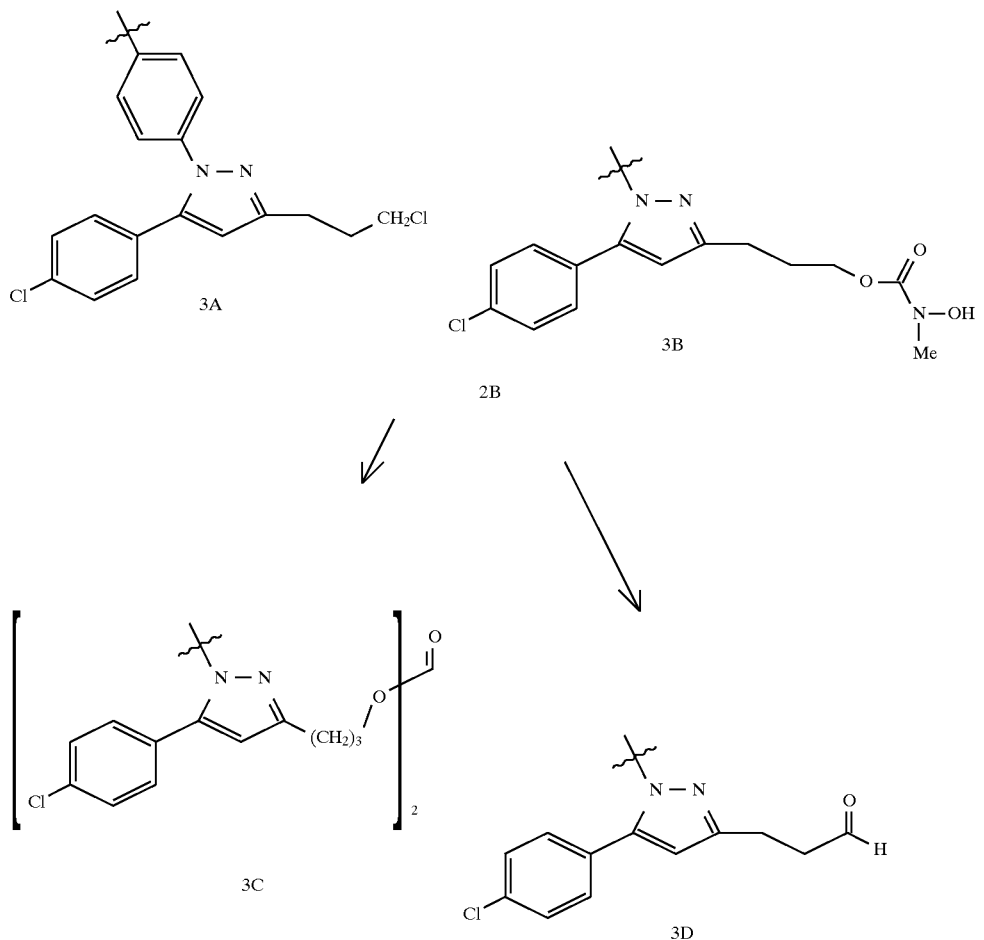

In order to prepare compounds where $R_5$ is $(CH_2)_2C(O)N(OH)CH_3$, Scheme 4 may be used. The acid, 2A, may be treated with carbonyldiimidazole (ca. 1.2 eq.) in $CH_2Cl_2$ at room temperature for about 1 h, followed by treatment of the resulting mixture with N-methylhydroxylamine hydrochloride (ca. 1.2 eq.) and triethylamine (ca. 1.2 eq.) in $CH_2Cl_2$ at room temperature for about 4 days to give the hydroxamic acid 4A. Scheme 4 also illustrates the synthesis of compounds where $R_5$ is $(CH_2)_2C(N)$—OH. Aldehyde 3D is treated with N-hydroxylamine hydrochloride (3 eq.) and sodium acetate (3 eq.) in EtOH at room temperature to reflux over 3 h to give the desired oxime 4B.

SCHEME 4

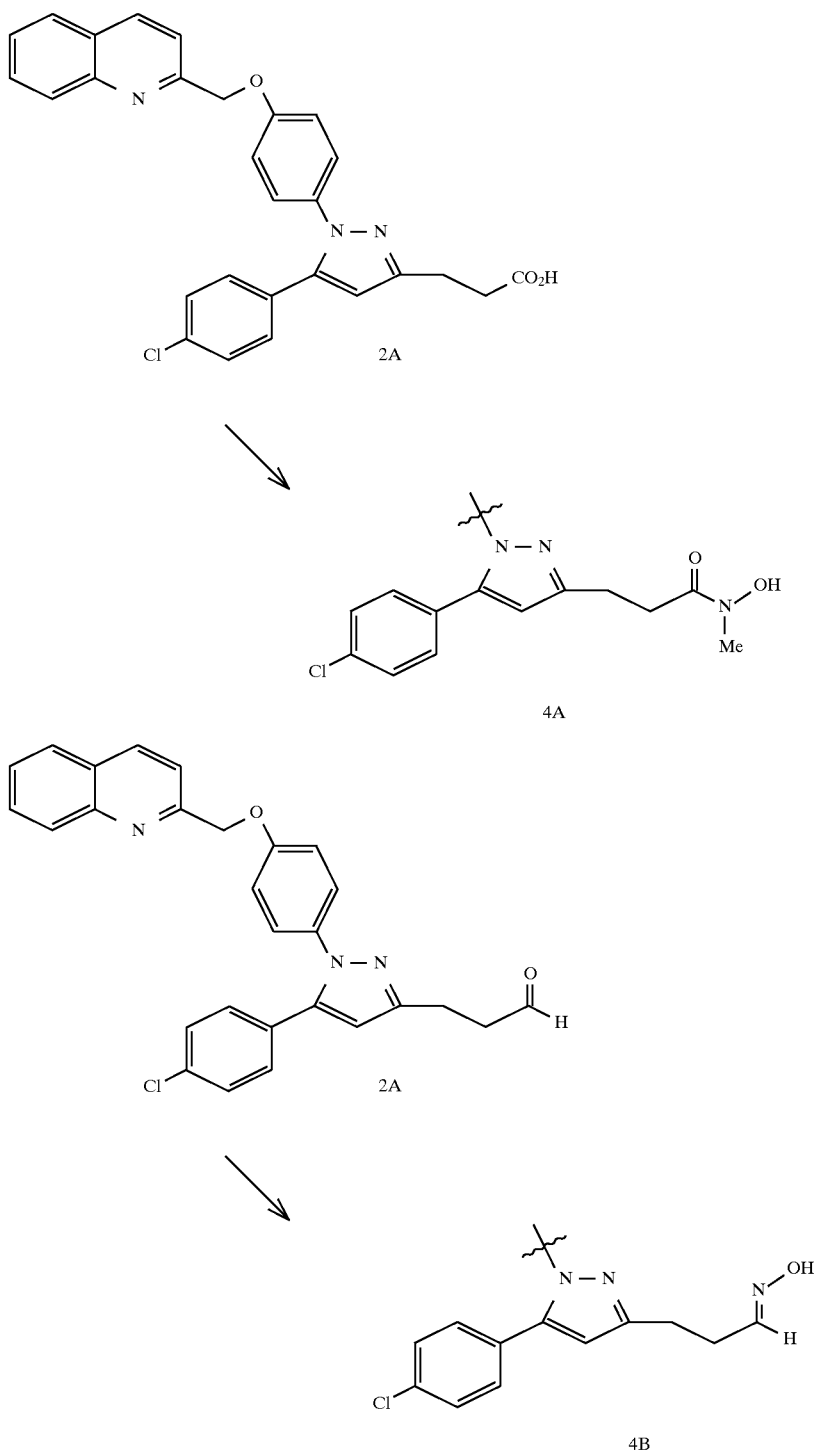

To prepare the compounds of Formula 1 where $R_5$ is $CH_2CH—(CO_2Me)$-4-(2-quinolinmethoxy)phenyl), Scheme 5 may be used. Halide 5A (prepared via the method outlined in Scheme 3) is treated with NaH/THF and 1-[4-(2-quinolinmethoxy)phenyl]acetic acid methyl ester at 0° C. to room temperature to give compound 5B. In order to prepare compounds where $R_5$ is $(CH_2)_2CH—(CO_2Me)$-4-(2-quinolinmethoxy)phenyl), halides such as 3A can be substituted for 5A in Scheme 5.

The ester group of 5B may be treated in the same manner as 1C, to give compounds where $R_8$ is halo, oxy, hydroxy, oximino, carboxy and $N—C_{1-5}$alkyl-N-hydroxyamido

SCHEME 5

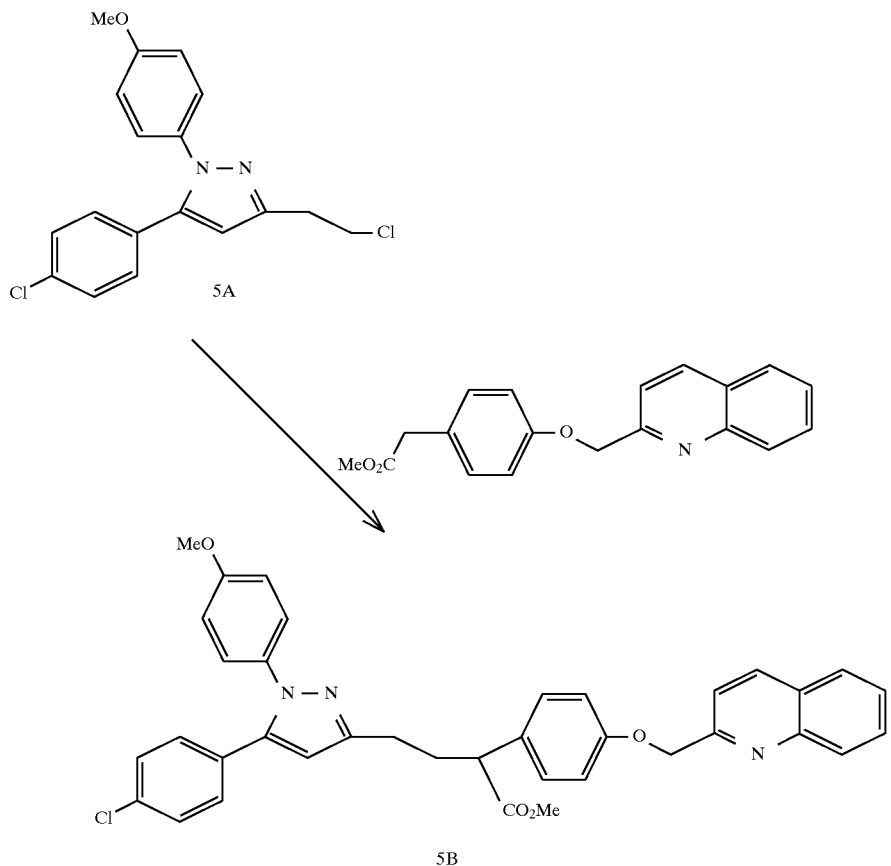

To prepare compound where $R_5$ is $C_{1-5}$alkyl, Scheme 6 may be used. The dione 6A is treated with an appropriately substituted hydrazine hydrochloride, 6B, in an alcoholic solvent at room temperature to give the pyrazole 6C. This pyrazole may be treated with HBr, followed by coupling with 2-(chloromethyl)quinoline as described in Scheme 1 to give the desired compound 6D. Compound 6D may be used to prepared compounds where $R_6$ is halo. For example, treatment of 6D with NBS at room temperature for 16 h affords the bromide 6E.

SCHEME 6

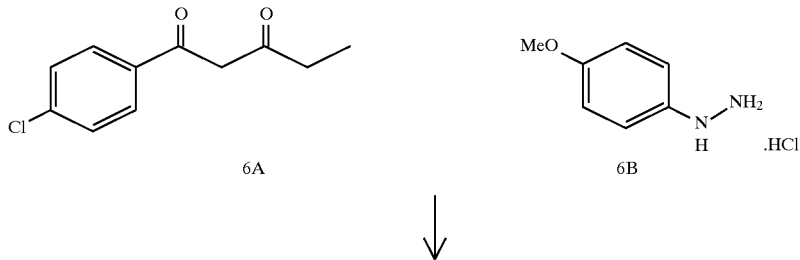

-continued
SCHEME 6

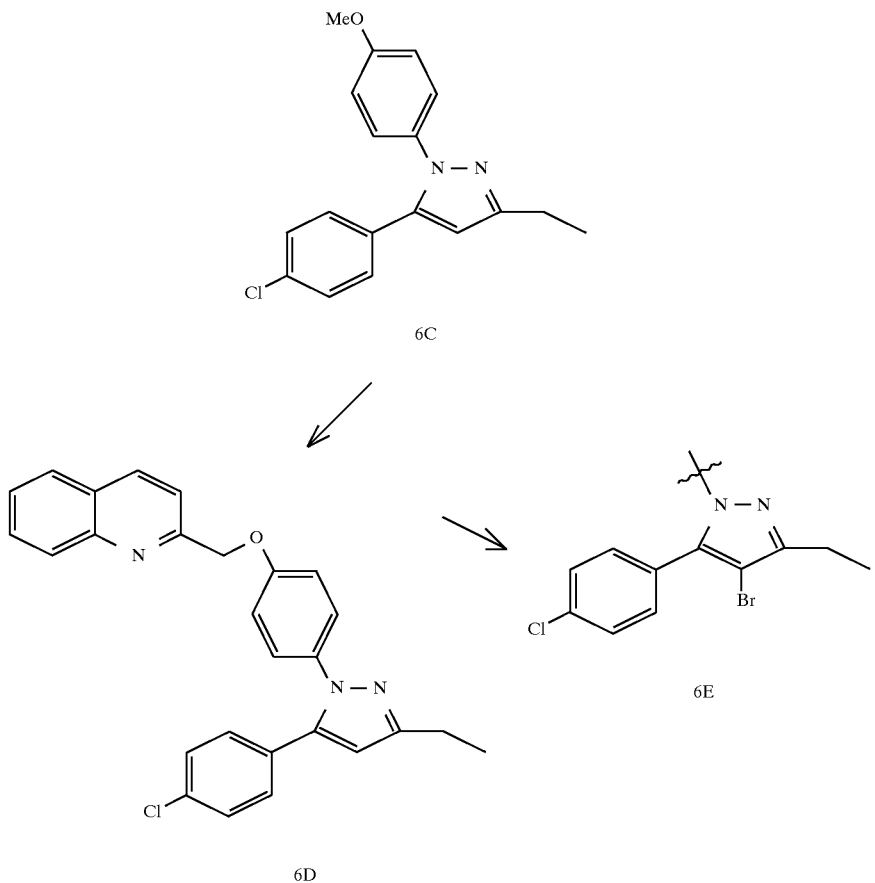

All compounds of Formula I may be prepared using the aforementioned schemes. For example, most of the starting materials which lead to different aromatic substitution on the 1 and 5 pyrazole positions (analogs of 1C) are made from the acids described in U.S. Pat. No. 4,826,868. However in order to make compounds where one of $R_1$, $R_2$, $R_3$ or $R_4$ are hydroxy, Scheme 7 may be used. An appropriately substituted hydrazine, 7B is treated with 1-(4-benzyloxyphenyl)-6-carboxyhexan-1,3-dione, 7A at room temperature in an alcoholic solvent to give the pyrazole 7C. This compound is debenzylated with 10% Pd/C to give the hydroxy acid 7D. This compound may be treated with 2-(chloromethyl)quinoline as described in Scheme 1 to give 7E.

SCHEME 7

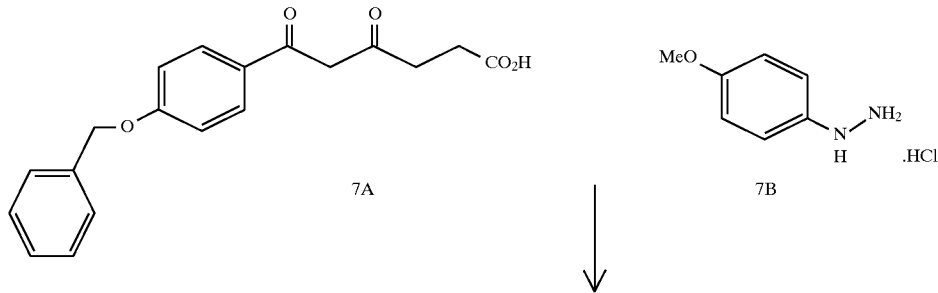

-continued
SCHEME 7

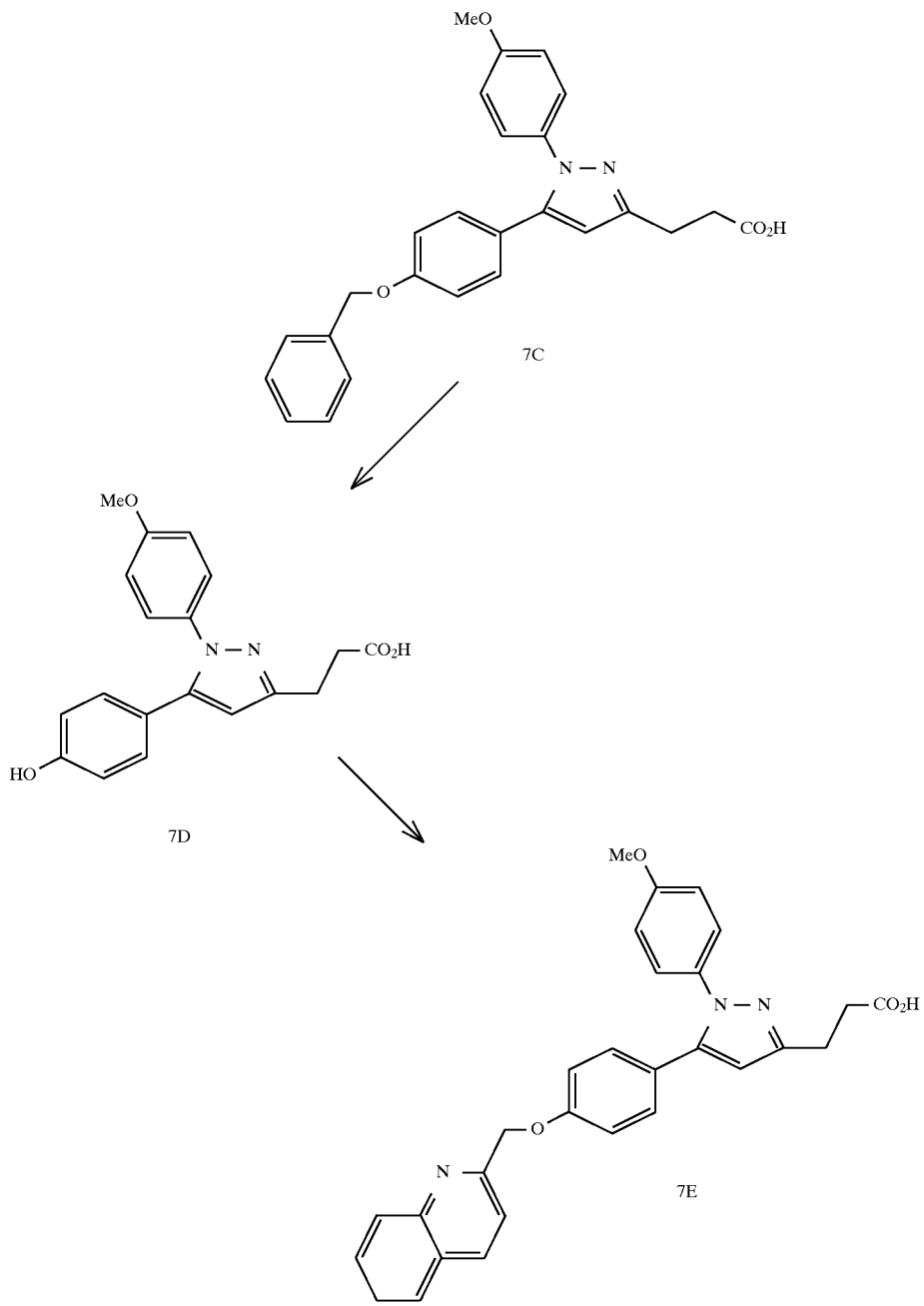

The preferred compositions of Formula I include compounds where:

R$_1$ and R$_3$ are: 4-halo, 4-(2-quinolinylmethoxy)phenyl, 4-hydroxy and C$_{1-5}$alkoxy;

R$_7$ is: (CH$_2$)$_n$R$_8$, where n is 2 and R$_8$ is carboxy, N—C$_{1-5}$alkyl-N-hydroxy-amido, C$_{1-5}$alkoxycarbonyl; or (CH$_2$)$_n$R$_8$R$_9$ where R$_9$ is 4-(2-quinolinylmethoxy)phenyl;

R$_6$ is hydrogen and C$_{1-5}$alkyl.

The compounds of the invention were evaluated for their ability to inhibit the production of the arachidonic acid product 5-HETE in broken and whole cell models. Since this is the first step of leukotriene biosynthesis, a reduction in the production of 5-HETE is directly attributable to inhibition of 5-lipoxygenase, where the standard concentration is 3.0 μM. If the IC$_{50}$ of the whole cell assay is smaller than the IC$_{50}$ of the broken cell model, it is an indication that the compounds are inhibiting the cooperation of FLAP and 5-lipoxygenase.

Rat basophilic leukemia cells (RBL-1; 5×10$^7$ viable cells/mL) were disrupted by homogenization on ice (four 20 sec bursts) with a Brinkman polytron. Complete cell breakage was verified microscopically. The homogenate was then centrifuged at 9,220×g for 48 minutes at 4° C. The pellet was discarded and the supernatant was saved as the source of enzymes. The supernatant was pre-incubated for five minutes at 37° C. in the presence of 2 mM of CaCl$_2$ and compound or vehicle (1% DMSO). The conversion of AA into products by CO and LO was initiated by adding 10 μL (50 μCi) of 1-$^{14}$C-AA to each tube and incubated at 37° C. for 20 minutes. The reaction was stopped by adjusting the pH of each sample to 3 to 3.5 with 2M formic acid. Samples were extracted with three volumes of chloroform to isolate the products of 5-LO formed during the reaction. Fractions were dried under nitrogen, then resuspended in 40 μL of chloroform and spotted onto silica gel HL plates. The plates were developed in A-9 solvent. The dried plates were analyzed using a Bioscan Imaging TLC scanner to determine the percentage of radiolabelled M converted to 5-HETE (LO product) in each sample. The percentage of inhibition was calculated by:

[1-(5-HETE test)]/5-HETE control×100=% inhibition

The IC$_{50}$ was determined using a curve fit in Cricket Graph (Computer Associated), which provided the equation of the regressed line used in the calculation.

The ability to inhibit 5-LO and CO in intact RBL-1 cells was also evaluated. RBL-1 cells were maintained in culture in minimal essential medium (Bio*Whittaker, Walkersville, Md.), containing 12.5% fetal calf serum, 10 mg/mL streptomycin, 10 I.U./mL penicillin G, 50 mg/mL gentamycin and 2 mM L-glutamine (Bio*WNhittaker, Walkersville, Md.). Cells were collected by centrifugation, washed once in HBSS, and resuspended at a concentration of 1×10$^5$ cells/mL. Cells were incubated in the presence of vehicle or drug then centrifuged at 800×g for 10 minutes at 4° C. The supernatant was removed by aspiration and the cells were resuspended in 0.5 mL of HBSS. The reaction was started by the addition of 20 μg/mL of calcium ionophore A 23187 (mixed calcium and magnesium salts, Calbiochem, La Jolla Calif.) and allowed to proceed for 15 minutes, then stopped by plunging the tubes into a slush ice bath. The conversion of AA to 5-LO products was initiated by the addition of 10 μL (50 uCi) of 1-$^{14}$C-AA. Products were isolated by acidification and extraction, followed by thin layer chromatography analysis as described above. Radioactive areas corresponding to authentic 5-LO (5-HETE) and CO (PGD$_2$) products were quantitated by the Bioscan 2000 Imaging System and the IC50 was calculated as above.

The % inhibition and IC50 values at a dose of 3 μM for representative compounds are listed in Tables A and B

TABLE A

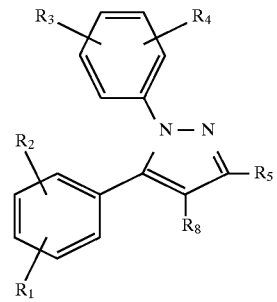

QM = 2-quinolinylmethoxy

| | | | | Isolated Enzyme | | Whole Cell |
|---|---|---|---|---|---|---|
| Cpd # | R$_1$ | R$_3$ | R$_5$ | % Inhib. | IC$_{50}$ μM | IC$_{50}$ μM |
| 1 | 4-Cl | 4-QM | —CH$_2$CO$_2$Et | 29 | | 13.4 |
| 2 | 4-Cl | 4-QM | —CH$_2$CO$_2$H | 15 | | 0.39 |
| 3 | 4-Cl | 4-QM | —(CH$_2$)$_2$OH | 31 | | 1.3 |
| 4 | 4-Cl | 4-QM | —(CH$_2$)Cl | 55 | | 5.3 |
| 5 | 4-Cl | 4-QM | (CH$_2$)$_2$O$_2$CN(Me)OH | 93 | | 1.1 |
| 7 | 4-Cl | 4-QM | (CH$_2$)$_2$CON(Me)OH | 93 | 0.21 | 0.49 |
| 8 | 4-Cl | 4-QM | (CH$_2$)$_2$CHO | 49 | | 3.2 |
| 9 | 4-Cl | 4-QM | (CH$_2$)$_2$CH(N)OH | 44 | | 0.55 |
| 10 | 4-Cl | 4-QM | —(CH$_2$)$_2$CO$_2$iso-Bu | 34 | | 1.5 |
| 11 | 4-Cl | 4-QM | Me | 32 | | 6.5 |
| 12 | 4-Cl | 4-QM | —(CH$_2$)$_2$CO$_2$Et | 19 | | 7.4 |
| 13 | 4-QM | 4-OMe | —(CH$_2$)$_2$CO$_2$H | 8 | | 3.9 |
| 14 | 4-QM | 4OMe | —(CH$_2$)$_2$CO$_2$H | 24 | | 2 |
| 15 | 4-Cl | 4-QM | —(CH$_2$)$_2$CO$_2$H | 0 | | 5.2 |
| 16 | 4-QM | 4OMe | (CH$_2$)$_2$CON(Me)(OH) | 87 | | 0.54 |
| 17 | 4-QM | 4-H | —(CH$_2$)$_2$CO$_2$Me | 19 | | not tested |
| 18 | 4-QM | 4-Cl | —(CH$_2$)$_2$CO$_2$H | 0 | | not tested |
| 19 | 4-QM | 4-H | —(CH$_2$)$_2$CO$_2$H | 0 | | not tested |
| 20 | 4-Cl | 4-QM | —(CH$_2$)$_3$OH | 21 | | 0.84 |
| 21 | 4-QM | 4-Cl | —(CH$_2$)$_2$CON(Me)OH | 15 | | not tested |
| 22 | 4-Cl | 4-QM | —(CH$_2$)$_2$CON(Me)OH | 100 | | 1 |

TABLE B

| Cpd # | R₁ | R₃ | R₈ | Isolated Enzyme % Inhib. | Isolated Enzyme IC₅₀ μM | Whole Cell IC₅₀ μM |
|---|---|---|---|---|---|---|
| 22 | 4-Cl | 4-OMe | CO₂Me | 35 | 47.5 | 0.63 |
| 23 | 4-Cl | 4-OMe | CON(Me)OH | 73 | 5.3 | 0.52 |

As indicated by tables A and B the compounds of Formula I may be used in pharmaceutical compositions to treat patients (humans and other primates) with inflammatory related disorders, in the same manner as known 5-lipoxygenase inhibitors. The compounds can be administered by any parenteral route (intravenous, intraperitoneal, subcutaneous, dermal patch), or by an oral route where the preferred route is oral and the dosage range is 1–25 mg/kg.

The pharmaceutical compositions can be prepared using conventional pharmaceutical excipients and compounding techniques. Oral dosage forms may be elixers, syrups, capsules tablets and the like. Where the typical solid carrier is an inert substance such as lactose, starch, glucose, methyl cellulose, magnesium sterate, dicalcium phosphate, mannitol and the like; and typical liquid oral excipients include ethanol, glycerol, water and the like. All excipients may be mixed as needed with disintegrants, diluents, granulating agents, lubricants, binders and the like using conventional techniques known to those skilled in the art of preparing dosage forms. Parenteral dosage forms may be prepared using water or another sterile carrier.

Compounds of Formula I, may be isolated and used as their pharmaceutically acceptable salts. Examples of such salts include hydrobromic, hydroiodic, hydrochloric, perchloric, sulfuric, maleic, fumaric, malic, tartatic, citric, benzoic, mandelic, methanesulfonic, hydroethanesulfonic, benzenesulfonic, oxalic, pamoic, 2-naphthalenesulfonic, p-toluenesulfonic, cyclohexanesulfamic and saccharic.

The following representative examples are illustrative not limiting. Other embodiments which are included within the scope of this invention will be apparent to those skilled in the art of chemical synthesis and antiinflammatory agents.

EXAMPLES

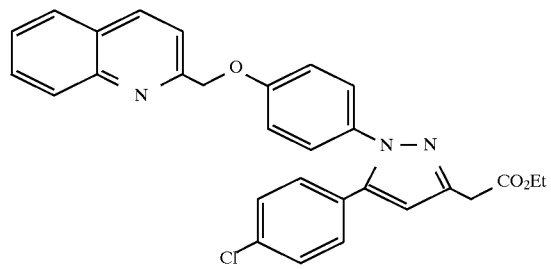

Example 1
Preparation of Ethyl [5-(4-Chlorophenyl)-1-(4-(2-quinolyl)methoxy)phenyl)-pyrazol-3-yl] acetate
Cpd 1

Ethyl [5-(4-Chlorophenyl)-1-(4-hydroxyphenyl)pyrazol-2-yl] acetate (3.92 g, 11 mmol), 2-(chloromethyl)quinoline. HCl (4.7 g, 1.5 eq.), K₂CO₃ (3.04 g, 1.5 eq.) and NaI (1.65 g, 1 eq.) were heated and stirred at reflux under N₂ for 5 days. The resulting mixture was concentrated in vacuo, dispersed in ethyl acetate, H₂O and 1N HCl. The resulting aqueous layer was extracted with several portions of ethyl acetate and the combined organic extracts were dried (Na₂SO₄) and concentrated in vacuo. The residue was purified by column chromatography and recrystallization to give the title compound as a white solid. mp 122°–123° C.

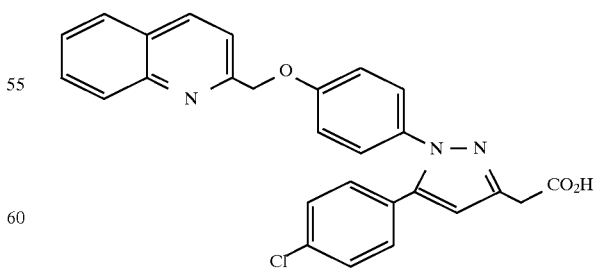

Example 2

Preparation of 2-[5-(4-Chlorophenyl)-1-(4-(2-quinolyl)methoxyphenyl)-pyrazol-3-yl]acetic acid Cpd 2

Cpd 1 (2.2 g, 4.4 mmol) and 2N NaOH (20 mL) were heated in EtOH to reflux under $N_2$. 3N HCl (30 mL) was added to the resulting mixture, which afforded a solid precipitate upon cooling. The off white solid was isolated and dried in vacuo to give the title compound. mp 228°–30° C.

Example 3

Preparation of 2-[5-(4-Chlorophenyl)-1-(4-(2-quinolyl)methoxy)phenyl)-pyrazol-3-yl]ethanol Cpd 3

Diisobutylaluminum hydride (DIBAL) (12 mL, 3 eq.) was added slowly to a stirred solution of Cpd 1 (2.01 g, 4 mmol) in THF (25 mL) at 0° C. After the addition, the mixture was allowed to warm to room temperature for about 3 h and concentrated in vacuo. A portion of $H_2O$ (150 mL) was added and this aqueous layer was extracted with several portions of ethyl acetate. The combined organic extracts were dried, ($Na_2SO_4$) and concentrated in vacuo. The residue was recrystallized from ethyl acetate and hexanes to give the title compound as an off-white solid. mp 130°–32° C.

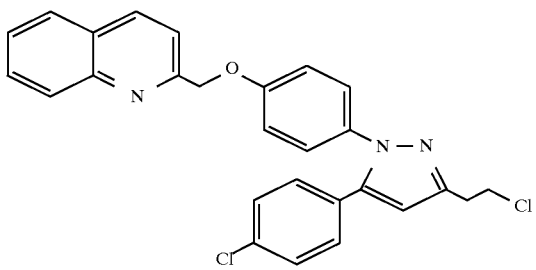

Example 4

Preparation of 3-(2-Chloroethyl)-5-(4-chlorophenyl)-1-[4-(2-quinolyl)methoxyphenyl]pyrazole Cpd4

A solution of triphosgene (0.79 g, 2.8 mmol) in $CH_2Cl_2$ (15 mL) was added to a stirred solution of Cpd 3 (2.4 g, 5 mmol) and pyridine (0.4 mL 5 mmol) in $CH_2Cl_2$ (30 mL). This mixture was stirred for 1 h at room temperature and concentrated in vacuo. The residue was added to a mixture of methyl hydroxylamine hydrochloride (0.84 g, 2 eq.) and triethylamine (1.4 mL, 2.0 eq.) in $CH_2Cl_2$ (25 mL) at 0° C., and the resulting mixture was allowed to warm up to room temperature and stirred overnight. The reaction mixture was partitioned between $H_2O$ and ethyl acetate and the resulting aqueous layer was washed with several portions of ethyl acetate. The combined organic extracts were dried ($Na_2SO4$) and concentrated in vacuo. The residue was purified by column chromatography and recrystallization to give the title compound as an off-white solid. mp 105°–08° C.

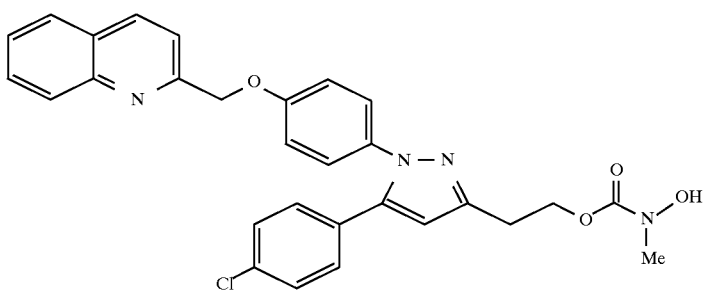

Example 5

Preparation of 5-(4-Chlorophenyl)-3-[2-(N-hydroxy-N-methylcarbamoyloxy)]-ethyl]-1-[4-(2-quinolyl)methoxyphenyl]pyrazole.0.05 Hydrate Cpd 5

The title compound was isolated from the purification (column chromatography of Cpd 4 as a yellow oil. Rf.=0.73.

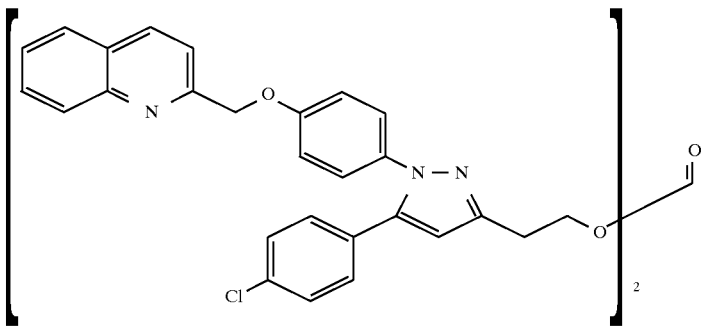

Example 6

Preparation of Di-2-{5-(4-Chlorophenyl)-1-[4-(2-quinolyl)methoxyphenyl]-pyrazol-3-yl} ethylcarbonate Cpd 6

Cpd 3 (1.09 g, 2.4 mmol) and triphosgene (0.35 g, 1.2 mmol) in pyridine (20 mL) were combined at 0° C., stirred at room temperature for 3 h and concentrated in vacuo. A solution of N-methylhydroxylamine (0.8 g, 4 eq.) and triethylamine (1.34 mL, 4 eq.) in $CH_2Cl_2$ (35 mL) was added to the residue and the resulting mixture was stirred for 7 days at room temperature. The reaction was quenched with $H_2O$ (150 mL) and extracted with several portions of $CH_2Cl_2$. The combined organic extracts were dried ($Na_2SO_4$) and purified by column chromatography using $CH_2Cl_2$/MeOH as an eluent to give a brown oil. IR (KBr cm$^{-1}$ 1744, 1514.

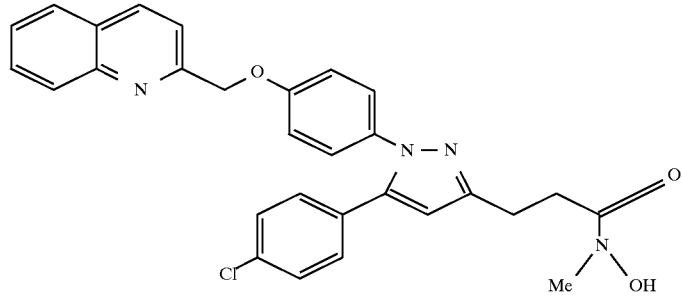

Example 7

Preparation of 3-{5-(4-Chlorophenyl)-N-hydroxy-N-methyl-1-[4-(2-quinolyl)methoxyphenyl]pyrazol-3-yl}propanamide Cpd 7

Neat oxalyl chloride (0.29 mL, 3.3 mmol) in $CH_2Cl_2$ (15 mL) was added to a solution of 3-[5-(4-chlorophenyl)-1-(4-(2-quinolyl)methoxyphenyl)-pyrazol-3-yl]propionic acid (0.9 g, 3.3 mmol: prepared in the manner of Cpd 2) in $CH_2Cl_2$ (30 mL) at 0° C. This mixture was stirred at room temperature for 4 h concentrated in vacuo and the residue was dissolved in $CH_2Cl_2$ (25 mL). This solution was added to a solution of N-methylhydroxylamine hydrochloride (0.31 g, 3.72 mmol), and triethylamine (0.52 mL, 3.72 mmol) in $CH_2Cl_2$ (40 mL) at 0° C. and the resulting mixture was allowed to warm up to room temperature overnight. The reaction was quenched with 1N HCl (50 mL) and extracted with several portions of $CH_2Cl_2$. The combined organic layers were dried ($Na_2SO_4$) and concentrated in vacuo. The residue was purified by column chromatography (ethyl acetate eluent) and recrystallization (ethyl acetate/$CH_2Cl_2$) to give the title compound as a white solid mp 130°–31° C.

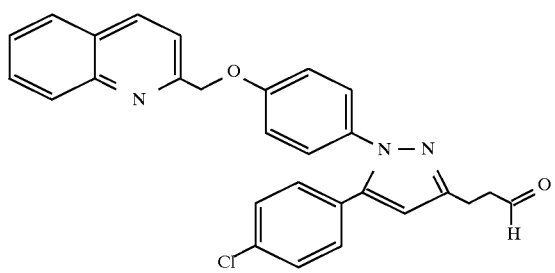

Example 8

Preparation of 3-[5-(4-Chlorophenyl)-1-(4-(2-quinolyl)methoxy)phenyl)-pyrazol-3-yl]propanal Cpd 8

A mixture of 3-[5-(4-chlorophenyl)-1-(4-(2-quinolyl)methoxy)phenyl)pyrazol-3-yl]propanol (6.46 g, 13.75 mmol: prepared in the manner of Cpd 3) and PCC (5.93 g, 27.5 mmol) in $CH_2Cl_2$ (30 mL) was stirred at room temperature for 2 h. The solvent was decanted and the precipitate was washed with several portions of ethyl acetate. The combined organic washings were filtered through paper and a florisil column and finally concentrated in vacuo. The residue was purified by column chromatography (ethyl acetate/hexanes) and recrystallizations from $Et_2O$ to give the title compound as a white solid. mp 85°–89° C.

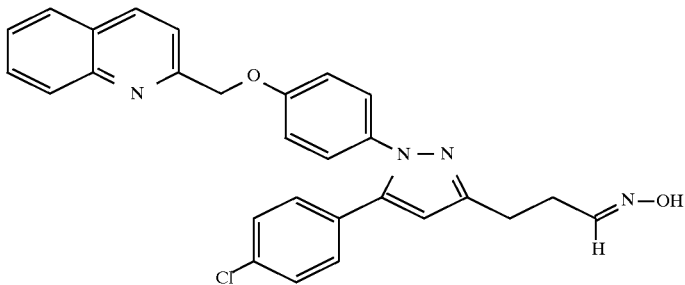

Example 9

Preparation of 5-(4-Chlorophenyl)-3-oximino 1-(4-(2-quinolyl)methoxy)phenyl)-pyrazol-3-yl]propanal. 0.25 Hydrate Cpd 9

A mixture of Cpd 8 (0.9 g, 1.9 mmol), hydroxylamine (0.79 g, 5.7 mmol) and sodium acetate (0.94 g, 5.7 mmol) in EtOH (20 mL) was stirred at room temperature for 2 h and heated to reflux for 1 h. The mixture was concentrated in vacuo, quenched with $H_2O$ (250 mL) and extracted with several portions of ethyl acetate The combined organic extracts were dried and concentrated in vacuo to give an oil which crystallized upon standing to give the title compound as a white solid. mp 139°–41° C.

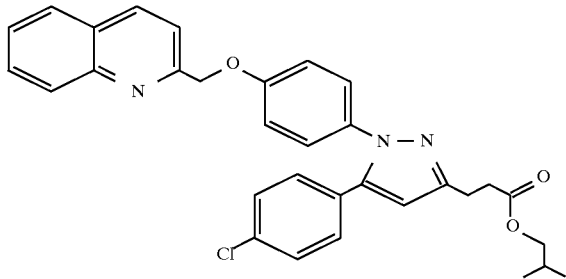

Example 10

3-{5-(4-Chlorophenyl)-N-hydroxy-N-methyl-1-[4-(2-quinolyl)methoxyphenyl]pyrazol-3-yl}propionate Cpd 10

Diisobutylaluminum hydride (58.75 mL, 19.5 mmol) was added slowly to a solution of ethyl [5-(4-Chlorophenyl)-1-(4-hydroxyphenyl)pyrazol-3-yl] propionate (10.0 g, 19.5 mmol: prepared in the manner of Cpd 1) in THF (25 mL) at 0° C. The resulting mixture was allowed to warm to room temperature and was stirred overnight and concentrated in vacuo. The residue was cooled, $H_2O$ (500 mL) was added and the mixture was extracted with several portions of ethyl acetate. The combined extracts were dried and concentrated in vacuo. The residue was purified by recrystallization from ether/hexane to give the title compound as a white solid. mp 95°–97° C.

We claim:

1. A compound selected from those of Formula II

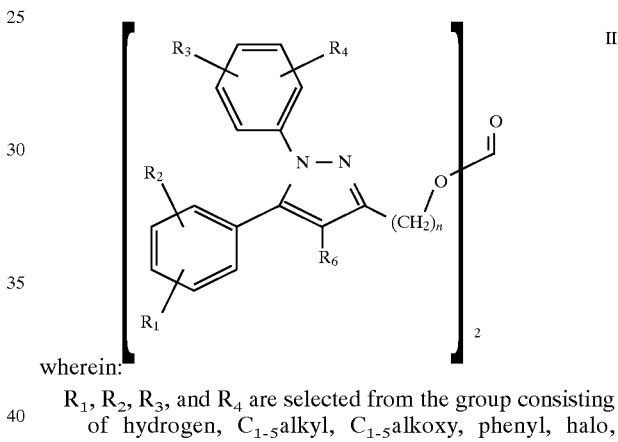

wherein:

$R_1$, $R_2$, $R_3$, and $R_4$ are selected from the group consisting of hydrogen, $C_{1-5}$alkyl, $C_{1-5}$alkoxy, phenyl, halo, hydroxy, $C_{1-5}$alkylsulfonyl, $C_{1-5}$alkylthio, trihalo$C_{1-5}$alkyl, amino, nitro and 2-quinolinylmethoxy;

n is 1–3;

$R_6$ is selected from the group consisting of hydrogen, $C_{1-5}$alkyl and halo;

with the proviso that one of $R_1$, $R_2$, $R_3$, and $R_4$ is 2-quinolinylmethoxy and pharmaceutically acceptable salts thereof.

* * * * *